(12) United States Patent
Wu et al.

(10) Patent No.: US 8,445,290 B2
(45) Date of Patent: *May 21, 2013

(54) TEMPERATURE-ADJUSTED ANALYTE DETERMINATION FOR BIOSENSOR SYSTEMS

(75) Inventors: Huan-Ping Wu, Granger, IN (US); Christine D. Nelson, Edwardsburg, MI (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/413,028

(22) Filed: Mar. 6, 2012

(65) Prior Publication Data

US 2012/0215460 A1 Aug. 23, 2012

Related U.S. Application Data

(63) Continuation of application No. 12/839,643, filed on Jul. 20, 2010, now Pat. No. 8,148,162, which is a continuation of application No. 12/187,743, filed on Aug. 7, 2008, now Pat. No. 7,781,222, which is a continuation of application No. PCT/US2007/004712, filed on Feb. 23, 2007.

(60) Provisional application No. 60/776,986, filed on Feb. 27, 2006.

(51) Int. Cl.
*G01N 33/66* (2006.01)
*G01N 25/00* (2006.01)
*G01N 33/50* (2006.01)
*C12Q 1/54* (2006.01)

(52) U.S. Cl.
USPC .............. 436/147; 436/8; 436/14; 436/63; 436/95; 436/149; 436/150; 436/164; 422/82.01; 422/82.05; 422/82.12; 435/14

(58) Field of Classification Search
USPC .............. 436/8, 14, 63, 95, 147, 149, 150, 436/164; 422/68.1, 82.01, 82.02, 82.05, 82.09, 422/82.12, 400; 73/1.01, 1.02; 435/14; 708/205
See application file for complete search history.

(56) References Cited

U.S. PATENT DOCUMENTS 4,431,004 A 2/1984 Bessman et al.
4,750,496 A 6/1988 Reinhart et al.
(Continued)

FOREIGN PATENT DOCUMENTS

JP 7198707 8/1995
RU 2202784 8/2002
(Continued)

OTHER PUBLICATIONS

International Searching Authority, "International Search Report and Written Opinion for PCT/US2007/004712", Jul. 20, 2010, Published in: EP.

*Primary Examiner* — Maureen Wallenhorst
(74) *Attorney, Agent, or Firm* — Blanchard & Associates

(57) ABSTRACT

A biosensor system determines analyte concentration from an output signal generated by an oxidation/reduction reaction of the analyte. The biosensor system adjusts a correlation for determining analyte concentrations from output signals at one temperature to determining analyte concentrations from output signals at other temperatures. The temperature-adjusted correlation between analyte concentrations and output signals at a reference temperature may be used to determine analyte concentrations from output signals at a sample temperature.

23 Claims, 7 Drawing Sheets

U.S. PATENT DOCUMENTS

| | | | |
|---|---|---|---|
| 5,366,609 A | 11/1994 | White et al. | |
| 5,395,504 A | 3/1995 | Saurer et al. | |
| 5,508,171 A | 4/1996 | Walling et al. | |
| 5,620,579 A | 4/1997 | Genshaw et al. | |
| 5,653,863 A | 8/1997 | Genshaw et al. | |
| 5,997,817 A | 12/1999 | Crismore et al. | |
| 6,153,069 A | 11/2000 | Pottgen et al. | |
| 6,233,471 B1 | 5/2001 | Berner et al. | |
| 6,391,645 B1 | 5/2002 | Huang et al. | |
| 6,413,411 B1 | 7/2002 | Pottgen et al. | |
| 6,576,117 B1 | 6/2003 | Iketaki et al. | |
| 7,338,639 B2 | 3/2008 | Burke et al. | |
| 7,781,222 B2 * | 8/2010 | Wu et al. | 436/147 |
| 8,148,162 B2 * | 4/2012 | Wu et al. | 436/147 |
| 2002/0019022 A1 | 2/2002 | Dunn et al. | |
| 2004/0256248 A1 | 12/2004 | Burke et al. | |
| 2004/0259270 A1 | 12/2004 | Wolf | |
| 2008/0179197 A1 * | 7/2008 | Wu | 205/775 |

FOREIGN PATENT DOCUMENTS

| | | |
|---|---|---|
| WO | 2004079797 | 9/2004 |
| WO | 2006079797 | 8/2006 |
| WO | 2007100651 | 9/2007 |

* cited by examiner

TEMPERATURE-ADJUSTED ANALYTE DETERMINATION FOR BIOSENSOR SYSTEMS

REFERENCE TO RELATED APPLICATIONS

This application is a continuation of U.S. application Ser. No. 12/839,643 entitled "Temperature-Adjusted Analyte Determination for Biosensor System" filed Jul. 20, 2010, now U.S. Pat. No. 8,148,162 issued on Apr. 3, 2012, which was a continuation of U.S. application Ser. No. 12/187,743 entitled "Temperature-Adjusted Analyte Determination for Biosensor System" filed Aug. 7, 2008, now U.S. Pat. No. 7,781,222, which was a continuation of PCT/US2007/004712 entitled "Temperature-Adjusted Analyte Determination for Biosensor Systems" filed Feb. 23, 2007, which was published in English and claimed the benefit of U.S. Provisional Application No. 60/776,986 entitled "Temperature-Adjusted Analyte Determination for Biosensor Systems" as filed on Feb. 27, 2006, each of which is incorporated herein by reference.

BACKGROUND

Biosensor systems usually provide an analysis of one or more analytes in biological fluids. The analysis typically includes a quantitative determination of the analyte in the biological fluid. The analysis is useful in the diagnosis and treatment of physiological abnormalities. For example, the determination of the glucose level in blood is important to diabetic individuals who frequently check their blood glucose level to regulate diet and/or medication. For other individuals, the monitoring of uric acid, lactate, cholesterol, bilirubin, and the like may be important.

Biosensor systems may be implemented using bench-top, portable, and other measuring devices. The portable devices may be hand-held and usually include a measuring device and a sensor strip. Typically, a sample of a biological fluid is introduced to the sensor strip, which is disposed in the measuring device for analysis. Biosensor systems may be designed to analyze one or more analytes and may use different volumes of biological fluids. Some biosensor systems may analyze a single drop of whole blood (WB), such as from 1-15 microliters (μL) in volume.

Biosensor systems usually measure an output signal to determine the analyte concentration in a sample of the biological fluid. The output signal is generated from an oxidation/reduction or redox reaction of the analyte. An enzyme or similar species may be added to the sample to enhance the redox reaction. The output signal may be an electric signal, light, or light converted to an electric signal. A biosensor system may generate the output signal using an optical sensor system or an electrochemical sensor system.

In optical systems, the analyte concentration is determined by measuring light that has interacted with a light-identifiable species, such as the analyte or a reaction or product formed from a chemical indicator reacting with the analyte redox reaction. An incident excitation beam from a light source is directed toward the sample. The light-identifiable species absorbs or shifts the wavelength of a portion of the incident beam, thus altering the wavelength or reducing the intensity of the incident beam. A detector collects and measures the attenuated or wavelength-altered incident beam, which is the output signal. In other optical systems, the chemical indicator fluoresces or emits light in response to the analyte redox reaction when illuminated by the excitation beam. A detector collects and measures the light, which is the output signal.

In electrochemical systems, the analyte concentration is determined by measuring an electrical signal, such as a current or potential. Typically, the analyte undergoes the redox reaction when an excitation signal is applied to the sample. The excitation signal usually is an electrical signal, such as a current or potential. The redox reaction generates an output signal in response to the excitation signal. The output signal usually is an electrical signal, such as a current or potential, which may be measured and correlated with the concentration of the analyte.

In electrochemical systems, the measuring device usually has electrical contacts that connect with electrical conductors in the sensor strip. The electrical connectors are connected by the conductors to electrodes that extend into the sample of the biological fluid. The measuring device applies the excitation signal through the electrical contacts to the electrical conductors, which convey the excitation signal into the sample through the electrodes. The redox reaction of the analyte generates an output signal in response to the excitation signal. The measuring device determines the analyte concentration in response to the output signal. Examples of portable measuring devices include the Ascensia Breeze® and Elite® meters of Bayer Corporation; the Precision® biosensors available from Abbott in Abbott Park, Ill.; Accucheck® biosensors available from Roche in Indianapolis, Ind.; and One-Touch Ultra® biosensors available from Lifescan in Milpitas, Calif. Examples of bench-top measuring devices include the BAS 100B Analyzer available from BAS Instruments in West Lafayette, Ind.; the CH Instruments' Electrochemical Workstation available from CH Instruments in Austin, Tex.; the Cypress Electrochemical Workstation available from Cypress Systems in Lawrence, Kans.; and the EG&G Electrochemical Instrument available from Princeton Research Instruments in Princeton, N.J.

Sensor strips may include reagents that react with the analyte in the sample of biological fluid. The reagents include an ionizing agent for facilitating the redox of the analyte, as well as any mediators or other substances that assist in transferring electrons between the analyte and the conductor. The ionizing agent may be an analyte specific enzyme, such as glucose oxidase or glucose dehydrogenase, to catalyze the oxidation of glucose in a WB sample. The reagents may include a binder that holds the enzyme and mediator together. In optical systems, the reagents include the chemical indicator along with another enzyme or like species to enhance the reaction of the chemical indicator with the analyte or products of the analyte redox reaction.

Most biosensor systems use correlation or calibration equations to determine the analyte concentration in a sample of a biological fluid. Correlation equations represent the relationship between output signals and analyte concentrations. From each correlation equation, an analyte concentration may be calculated for a particular output signal. The correlation equations are dependent on the temperature of the sample. The output signal for a particular analyte concentration may change due to the effect of temperature on the redox reaction of the analyte, enzyme kinetics, diffusion, and the like. A correlation equation may be needed for each possible sample temperature in order to calculate the analyte concentration from an output signal at a particular sample temperature.

To reduce the number of correlation equations used in the sample analysis, many biosensor systems attempt to provide analyte concentrations using one or more correlation equations for a particular reference temperature. The analyte concentration at a sample temperature usually is compensated for the difference between the sample temperature and the reference temperature to provide an analyte concentration at the reference temperature.

Some biosensor systems compensate for temperature by changing the output signal prior to calculating the analyte concentration from a correlation equation. The output signal usually is multiplied by a temperature correction coefficient or the like. The temperature-corrected output signal is used to determine the analyte concentration. Biosensor systems using a temperature-corrected output signal are described in U.S. Pat. Nos. 4,750,496 and 6,576,117.

Other biosensor systems compensate for temperature by changing the analyte concentration calculated by the correlation equation. The analyte concentration calculated from the correlation equation usually undergoes a temperature correction procedure to provide a temperature-corrected analyte concentration. Biosensor systems using a temperature-corrected analyte concentration are described in U.S. Pat. Nos. 5,366,609; 5,508,171; and 6,391,645.

Additional biosensor systems compensate for temperature by changing the output signal prior to calculating the analyte concentration from a correlation equation and/or by changing the analyte concentration calculated by the correlation equation. Biosensor systems using a temperature-corrected output signal and/or a temperature-corrected analyte concentration are described in U.S. Pat. Nos. 4,431,004 and 5,395,504.

While these temperature compensation methods balance various advantages and disadvantages, none are ideal. These methods may not fully incorporate various effects of different sample temperatures on the redox reaction of the analyte, the enzyme and mediator kinetics, and diffusion. These methods may not adequately address effects of different analyte concentrations on enzyme kinetics and diffusion at different sample temperatures. These methods also may not adequately address effects of different analyte concentrations on the redox reaction at different sample temperatures. In addition, the changes to the output signal and/or the calculated analyte concentration may introduce or magnify errors related to the determination of the analyte concentration from the output signal.

Accordingly, there is an ongoing need for improved biosensor systems, especially those that may provide increasingly accurate and precise analyte concentrations at a reference temperature. The systems, devices, and methods of the present invention overcome at least one of the disadvantages associated with conventional biosensor systems.

SUMMARY

The present invention provides a biosensor system that determines the analyte concentration in a sample of a biological fluid from an output signal generated by a redox reaction of the analyte. The biosensor system adjusts a correlation between analyte concentrations and output signals at a reference temperature to determine analyte concentrations from output signals at other temperatures. The biosensor system uses the temperature-adjusted correlation to determine the analyte concentration from an output signal at a sample temperature.

In a method for determining an analyte concentration in a sample of a biological fluid, the sample temperature is determined. An output signal is generated in response to a redox reaction of an analyte in the sample. A correlation between analyte concentrations and output signals at a reference temperature is adjusted in response to temperature. The analyte concentration is determined from the temperature-adjusted correlation and the output signal at the sample temperature.

In a method for adjusting a correlation between analyte concentrations and output signals at a reference temperature in response to temperature, the correlations between analyte concentrations and output signals are determined for a reference temperature and at least one other temperature. The normalized temperature functions of slope and intercept are developed for the correlation of the reference temperature. The correlation of the reference temperature is adjusted in response to the normalized temperature functions of slope and intercept.

A biosensor for determining an analyte concentration in a biological fluid includes a measuring device and sensor strip. The measuring device has a processor connected to a sensor interface and a temperature sensor. The sensor strip has a sample interface on a base. The sample interface is adjacent to a reservoir formed by the base. The processor adjusts a correlation between analyte concentrations and output signals at a reference temperature in response to a sample temperature from the temperature sensor. The processor determines an analyte concentration from the temperature-adjusted correlation in response to an output signal from the sample interface.

The following definitions are included to provide a clearer and more consistent understanding of the specification and claims.

"Analyte" is defined as one or more substances present in a sample. An analysis determines the presence and/or concentration of the analyte present in the sample.

"Sample" is defined as a composition that may contain an unknown amount of the analyte. Typically, a sample for electrochemical analysis is in liquid form, and preferably the sample is an aqueous mixture. A sample may be a biological sample, such as blood, urine, or saliva. A sample also may be a derivative of a biological sample, such as an extract, a dilution, a filtrate, or a reconstituted precipitate.

"Conductor" is defined as an electrically conductive substance that remains stationary during an electrochemical analysis.

"Accuracy" is defined as how close the amount of analyte measured by a sensor system corresponds to the true amount of analyte in the sample. Accuracy may be expressed in terms of the bias of the sensor system's analyte reading in comparison to a reference analyte reading. Larger bias values reflect less accuracy.

"Precision" is defined as how close multiple analyte measurements are for the same sample. Precision may be expressed in terms of the spread or variance among multiple measurements.

"Redox reaction" is defined as a chemical reaction between two species involving the transfer of at least one electron from a first species to a second species. Thus, a redox reaction includes an oxidation and a reduction. The oxidation half-cell of the reaction involves the loss of at least one electron by the first species, while the reduction half-cell involves the addition of at least one electron to the second species. The ionic charge of a species that is oxidized is made more positive by an amount equal to the number of electrons removed. Likewise, the ionic charge of a species that is reduced is made less positive by an amount equal to the number of electrons gained.

"Mediator" is defined as a substance that may be oxidized or reduced and that may transfer one or more electrons. A mediator is a reagent in an electrochemical analysis and is not the analyte of interest, but provides for the indirect measurement of the analyte. In a simplistic system, the mediator undergoes a redox reaction in response to the oxidation or reduction of the analyte. The oxidized or reduced mediator then undergoes the opposite reaction at the working electrode of the sensor strip and is regenerated to its original oxidation number.

"Binder" is defined as a material that provides physical support and containment to the reagents while having chemical compatibility with the reagents.

"Steady-state" is defined as when the change of a signal with respect to its independent input variable (time, etc.) is substantially constant, such as within ±10 or ±5%.

"Transient point" is defined as the value of a signal obtained as a function of time when an increasing rate of diffusion transitions into a relatively constant rate of diffusion. Before the transient point, the signal is rapidly changing with time. Similarly, after the transient point, the rate of signal decay becomes relatively constant, thus reflecting the relatively constant rate of diffusion.

"Handheld device" is defined as a device that may be held in a human hand and is portable. An example of a handheld device is the measuring device accompanying Ascensia® Elite Blood Glucose Monitoring System, available from Bayer HealthCare, LLC, Elkhart, Ind.

BRIEF DESCRIPTION OF THE DRAWINGS

The invention may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

A biosensor system that determines an analyte in a sample of a biological fluid is described. The biosensor system determines the analyte concentration from an output signal generated by an oxidation/reduction or redox reaction of the analyte. The system adjusts a correlation equation for determining analyte concentrations from output signals at one temperature to determining analyte concentrations from output signals at other temperatures, such as the sample temperature. The temperature-adjusted correlations improve the accuracy and precision of the biosensor system in determining the analyte concentration of the sample. The biosensor system may determine analyte concentrations from output signals at a sample temperature using a temperature-adjusted correlation equation for a reference temperature. The correlation equations between analyte concentrations and output signals may be represented graphically, mathematically, a combination thereof, or the like. The correlation equations may be represented by a program number (PNA) table, another look-up table, or the like. The biosensor system may be utilized to determine analyte concentrations such as glucose, uric acid, lactate, cholesterol, bilirubin, and the like.

Figure 1:
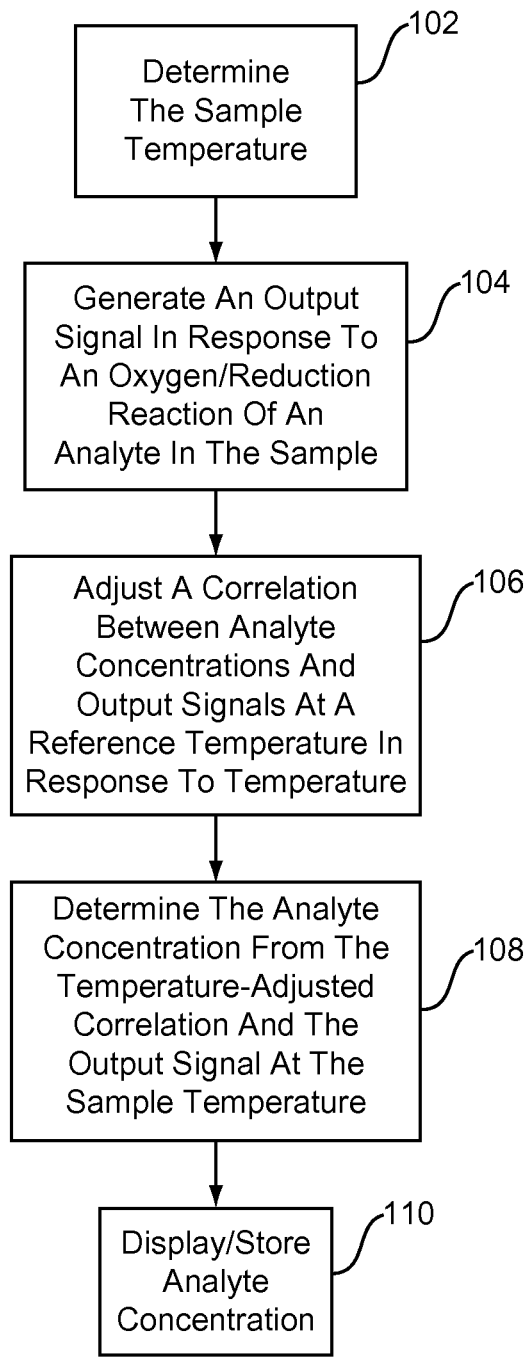
FIG. 1 represents a method for determining an analyte concentration in a sample of a biological fluid.

FIG. 1 represents a method for determining an analyte concentration in a sample of a biological fluid. In 102, the sample temperature is determined. In 104, an output signal is generated in response to an oxidation/reduction reaction of the analyte in the sample. In 106, a correlation between analyte concentrations and output signals at a reference temperature is adjusted in response to temperature. In 108, the analyte concentration is determined from the temperature-adjusted correlation and the output signal at the sample temperature. In 110, the analyte concentration is displayed and may be stored for future reference.

In 102 of FIG. 1, the sample temperature may be determined using various techniques. The sample temperature may be measured using a thermister, thermometer, or other temperature sensing device. The sample temperature may be calculated from the output signal of an electrochemical reaction in the sample. The sample temperature may be assumed to be the same or similar to a measurement of the ambient temperature or the temperature of a device implementing the biosensor system. Other techniques may be used to determine the sample temperature.

In 104 of FIG. 1, an output signal is generated in response to an oxidation/reduction or redox reaction of an analyte in the sample. The output signal may be generated using an optical sensor system, an electrochemical sensor system, or the like.

Optical sensor systems generally measure the amount of light absorbed or generated by the reaction of a chemical indicator with the analyte redox reaction. An enzyme may be included with the chemical indicator to enhance the reaction kinetics. The output signal or light from an optical system may be converted into an electrical signal such as current or potential.

In light-absorption optical systems, the chemical indicator produces a reaction product that absorbs light. A chemical indicator such as tetrazolium along with an enzyme such as diaphorase may be used. Tetrazolium usually forms formazan (a chromagen) in response to the redox reaction of the analyte. An incident excitation beam from a light source is directed toward the sample. The light source may be a laser, a light emitting diode, or the like. The incident beam may have a wavelength selected for absorption by the reaction product. As the incident beam passes through the sample, the reaction product absorbs a portion of the incident beam, thus attenuating or reducing the intensity of the incident beam. The incident beam may be reflected back from or transmitted through the sample to a detector. The detector collects and measures the attenuated incident beam (output signal). The amount of light attenuated by the reaction product is an indication of the analyte concentration in the sample.

In light-generated optical systems, the chemical detector fluoresces or emits light in response to the analyte redox reaction. A detector collects and measures the generated light (output signal). The amount of light produced by the chemical indicator is an indication of the analyte concentration in the sample.

Electrochemical systems apply an input signal to the sample of the biological fluid. The input signal may be a potential or current and may be constant, variable, or a combination thereof such as when an AC signal is applied with a DC signal offset. The input signal may be applied as a single pulse or in multiple pulses, sequences, or cycles. The analyte undergoes a redox reaction when the input signal is applied to the sample. An enzyme or similar species may be used to enhance the redox reaction of the analyte. A mediator may be used to maintain the oxidation state of the enzyme. The redox reaction generates the output signal that may be measured constantly or periodically during transient and/or steady-state output. Various electrochemical processes may be used such as amperometry, coulometry, voltammetry, or the like. Gated amperometry and gated voltammetry also may be used.

In amperometry, a potential or voltage is applied to a sample of the biological fluid. The redox reaction of the analyte generates a current in response to the potential. The current is measured over time to quantify the analyte in the sample. Amperometry generally measures the rate at which the analyte is oxidized or reduced to determine the analyte concentration in the sample. Biosensor systems using amperometry are described in U.S. Pat. Nos. 5,620,579; 5,653,863; 6,153,069; and 6,413,411.

In coulometry, a potential is applied to a sample of the biological fluid to exhaustively oxidize or reduce the analyte within the sample. The potential generates a current that is integrated over the time of oxidation/reduction to produce an electrical charge representing the analyte concentration. Coulometry generally captures the total amount of analyte within the sample. A biosensor system using coulometry for whole blood glucose measurement is described in U.S. Pat. No. 6,120,676.

In voltammetry, a varying potential is applied to a sample of biological fluid. The redox reaction of the analyte generates current in response to the applied potential. The current is measured over time to quantify the analyte in the sample. Voltammetry generally measures the rate at which the analyte is oxidized or reduced to determine the analyte concentration in the sample. Additional information about voltammetry may be found in "Electrochemical Methods: Fundamentals and Applications" by A. J. Bard and L. R. Faulkner, 1980.

In gated amperometry and gated voltammetry, pulsed excitations are used as described in U.S. Provisional Patent Application Nos. 60/700,787, filed Jul. 20, 2005, and 60/722,584, filed Sep. 30, 2005, respectively, which are incorporated by reference.

In 106 of FIG. 1, a correlation between analyte concentrations and output signals at a reference temperature is adjusted in response to temperature. The correlation may be represented by a correlation or calibration equation that calculates analyte concentrations from output signals at the reference temperature. The correlation equation for the reference temperature is adjusted to calculate analyte concentrations in response to output signals at other temperatures such as the sample temperature. The correlation equation may be for a reference temperature of 25° C. Correlation equations for other reference temperatures may be used.

The correlation equation may be implemented to manipulate the output signal for determination of the analyte concentration. The correlation equation also may be implemented as a program number assignment (PNA) table of the slope and intercept for the correlation equation, another look-up table, or the like for comparison with the electrical output signal to determine the analyte concentration.

The effect of temperature on the correlation or calibration equations is responsive to the behavior of diffusion and enzymatic reactions during the redox reaction. For example, temperature affects the oxidation and diffusion of glucose in a sample of whole blood. In addition, temperature affects the diffusion of optically active molecules.

The correlation equations may be linear or near linear, and may be described by a second order polynomial. In a general form, the correlation equation can be represented as follows:

$$OS = d_n * A^n + d_{n-1} * A^{n-1} + \ldots + d_2 * A^2 + d_1 * A + d_0 \quad (1).$$

Where A is the analyte concentration, OS is the output signal, and coefficients $d_n$, $d_{n-1}$, $d_2$, $d_1$, and $d_0$ describe a temperature dependent weighing factor for each term of the biosensor response.

The correlation equation may be described by the reverse expression, where the analyte concentration is expressed as a function of the output signal. This reduces the need to solve an $n^{th}$ order equation in order to find the analyte concentration. Thus, the correlation equation for analyte concentration may be represented as follows:

$$A = c_n * OS^n + c_{n-1} * OS^{n-1} + \ldots + c_2 * OS^2 + c_1 * OS + c_0 \quad (2).$$

Where $c_n$, $c_{n-1}$, $c_2$, $c_1$, and $c_0$ are coefficients that describe a temperature dependent weighing factor for each term of the biosensor response. The analyte concentration, A, may be glucose in a sample of whole blood. The output signal may be the current or potential of an electrochemical system, the absorbance or %-transmission of an optical system, or the like.

The correlation equation may be represented by a $2^{nd}$ order response between analyte concentration and output signals as follows:

$$A = c_2 * OS^2 + c_1 * OS + c_0 \quad (3).$$

The correlation equation may be represented by a linear response between analyte concentration and output signals as follows:

$$A_R = c_1 * OS_T + c_0 = OS_T / S_T + Int_T / S_T \quad (4).$$

Where $c_1 = 1/S_T$, $c_0 = Int_T / S_T$, and where $A_R$ is the analyte concentration at a reference temperature, $OS_T$ is the output signal, $S_T$ is the product of a slope at the reference temperature and a normalized temperature function of the slope, and $Int_T$ is the product of an intercept at the reference temperature and a normalized temperature function of the intercept.

Equation (4) may be rewritten to express the output signal in response to the analyte concentration as follows:

$$OS_T = S_T * A_R + Int_T \quad (5).$$

Where $OS_T$ is the output signal at another temperature such as the sample temperature, $A_R$ is the analyte concentration at the reference temperature, $S_T$ can be expressed as a product of a constant and a normalized temperature function of the slope, and $Int_T$ can be expressed as a product of a constant and a normalized temperature function of the intercept.

Equation (5) indicates that the output signal, $OS_T$, is a function of temperature in terms of the temperature effect on slope, $S_T$, and intercept, $Int_T$, under the analyte concentration, $A_R$. The slope, $S_T$, and intercept, $Int_T$, adjust the slope and intercept of a correlation equation at a reference temperature using normalized temperature functions of the slope and intercept. The temperature-adjusted slope and intercept of the correlation for the reference temperature may be used with an output signal at another temperature, such as the sample temperature, to calculate an analyte concentration.

Accordingly, the correlation equation (5) may be rewritten to calculate analyte concentrations using the temperature-adjusted slope and intercept of the correlation for the reference temperature and output signals at another temperature, as follows:

$$A_R = \frac{OS_T - Int_T}{S_T}. \tag{6}$$

Where $A_R$ is the analyte concentration at the reference temperature, $OS_T$ is the output signal at the other temperature, $Int_T$ is the intercept of the correlation for the reference temperature adjusted by a normalized temperature function for the intercept in response to the other temperature, and $S_T$ is the slope of the correlation for the reference temperature adjusted by a normalized temperature function for the slope in response to the other temperature.

The slope of the correlation for the reference temperature is adjusted in response to the sample temperature, as follows:

$$S_T = S_R * f(T) \tag{7}$$

Where $S_R$ is the slope of the correlation for the reference temperature and $f(T)$ is a temperature function that adjusts the slope for the sample temperature.

The temperature function of slope, $f(T)$, adjusts the slope of the correlation for the reference temperature to the slope of a correlation for another temperature. The temperature-adjusted slope may be used to calculate the analyte or glucose concentration using an output signal or current generated at the other temperature. To develop the temperature function of slope, $f(T)$, the slopes of correlations for other temperatures are normalized to the slope of the correlation for the reference temperature. The normalized slope of a correlation for a particular temperature is a unitless coefficient that adjusts the slope of the correlation for the reference temperature to the slope of the correlation for the particular temperature. The normalized slope of the correlation for the reference temperature is essentially one, indicating there is little or no adjustment to the slope of the correlation for the reference temperature. The normalized slopes are analyzed graphically and/or mathematically such as with a regression analysis to develop the temperature function of slope, $f(T)$. Another normalization method may be used to develop the temperature function.

The temperature function of slope, $f(T)$, may be a second order polynomial such as follows:

$$f(T) = a_2 T^2 + a_1 T + a_0 \tag{8}$$

Where T is the sample temperature and $a_2$, $a_1$, and $a_0$ are coefficients of a regression analysis representing the normalized slopes. While represented as a polynomial, the temperature function of slope, $f(T)$, may be represented as a constant, an exponential, trigonometric, or other function, a combination thereof, and the like.

The intercept of the correlation for the reference temperature is adjusted in response to the sample temperature, as follows:

$$Int_T = Int_R * g(T) \tag{9}$$

Where $Int_R$ is the intercept of the correlation for the reference temperature and $g(T)$ is a temperature function that adjusts the intercept for the sample temperature.

The temperature function of intercept, $g(T)$, adjusts the intercept of the correlation for the reference temperature to the intercept of a correlation for another temperature. The temperature-adjusted intercept may be used to calculate the analyte or glucose concentration using an output signal or current generated at the other temperature. To develop the temperature function of intercept, $g(T)$, the intercepts of correlations for different temperatures are normalized to the intercept of the correlation for the reference temperature. The normalized intercept of a correlation for a particular temperature is a unitless coefficient that adjusts the intercept of the correlation for the reference temperature to the intercept of the correlation for the particular temperature. The normalized intercept of the correlation for the reference temperature is essentially one, indicating there is little or no adjustment to the intercept of the correlation for the reference temperature. The normalized intercepts are analyzed graphically and/or mathematically such as with a regression analysis to develop the temperature function of intercept, $g(T)$. Another normalization method may be used to develop the temperature function.

The temperature function of intercept, $g(T)$, may be a second order polynomial such as follows:

$$g(T) = b_2 T^2 + b_1 T + b_0 \tag{10}$$

Where T is the sample temperature and $b_2$, $b_1$, and $b_0$ are coefficients of a regression analysis representing the normalized intercepts. While represented as a polynomial, the temperature function of intercept, $g(T)$, may be represented as a constant, an exponential, trigonometric, or other function, a combination thereof, and the like.

In 108 of FIG. 1, the analyte concentration of the sample is determined from the temperature-adjusted correlation equation (6) and the output signal at the sample temperature. The temperature functions of slope and intercept, $f(T)$ and $g(T)$, are calculated using equations (8) and (10), respectively. $S_T$ and $Int_T$, the slope and intercept of the correlation for the reference temperature adjusted in response to the sample temperature, are calculated using equations (7) and (9), respectively.

In 110 of FIG. 1, the analyte concentration calculated using temperature-adjusted correlation equation (6) and the output signal at the sample temperature may be displayed or stored for future reference.

The effect of changes in the slope and intercept on analyte concentration in relation to temperature changes may be analyzed. Temperature coefficients define the change in a parameter in relation to the change in temperature. For parameters such as analyte concentration, slope, and intercept, temperature coefficients may be defined as follows:

$$\alpha_A = \frac{\partial A/A}{\partial T} = \frac{\Delta A/A}{\Delta T}. \tag{11}$$

$$\alpha_S = \frac{\partial S/S}{\partial T} = \frac{\Delta S/S}{\Delta T}. \tag{12}$$

-continued $$\alpha_{Int} = \frac{\partial Int/Int}{\partial T} = \frac{\Delta Int/Int}{\Delta T}. \quad (13)$$

Where $\alpha_A$, $\alpha_S$, and $\alpha_{Int}$ are the temperature coefficients of the analyte concentration, slope, and intercept respectively, A is the analyte concentration, S is the slope, Int is the intercept, and T is temperature.

For a constant input signal such as current, the relative change in the analyte concentration, A, in relation to changes in the slope, S, and intercept, Int, may be given as follows using the analyte calculation equation (6) as follows:

$$dA = \frac{\partial A}{\partial S}dS + \frac{\partial A}{\partial Int}dInt. \quad (14)$$

$$\frac{dA}{A} = \left[\frac{\partial A}{\partial S}dS + \frac{\partial A}{\partial Int}dInt\right]/A. \quad (15)$$

$$\frac{\partial A}{\partial S} = \frac{OS - Int}{S}(-1/S) = -\frac{A}{S}. \quad (16)$$

$$\frac{\partial A}{\partial Int} = -1/S. \quad (17)$$

Where OS is an output signal such as current.

Substituting equations (16) and (17) into equation (15), gives the following relationships for the relative change in an analyte concentration such as glucose:

$$\frac{dA}{A} = -\frac{dS}{S} - \frac{dInt}{(S*A)}. \quad (18)$$

$$\frac{\Delta A}{A} = -\frac{\Delta S}{S} - \frac{\Delta Int}{(S*A)} = -\frac{\Delta S}{S} - \left[\frac{Int/S}{A}\right]*\left[\frac{\Delta Int}{Int}\right]. \quad (19)$$

Substituting the temperature coefficients from equations (11), (12), and (13) and translating equation (19) provides the following relationships:

$$\frac{\Delta A/A}{\Delta T} = -\frac{\Delta S/S}{\Delta T} - \left[\frac{Int/S}{A}\right]*\left[\frac{\Delta Int/Int}{\Delta T}\right]. \quad (20)$$

$$\frac{\Delta A/A}{\Delta T} = \alpha_A = -\alpha_S - \left[\frac{Int/S}{A}\right]*\alpha_{int}. \quad (21)$$

Equation (21) indicates that the effect of the temperature coefficient of slope is equivalent to the analyte concentration, but is opposite in magnitude. However, the effect of the temperature coefficient of intercept may be smaller in magnitude, depending on the slope, intercept, and analyte concentration being measured.

For an analyte such as glucose in whole blood, the effect of changes in the intercept temperature coefficient on the glucose temperature coefficient is small at higher glucose concentrations. If the ratio of intercept to slope, Int/S, is 50 and the glucose concentration is 150 mg/dL, only one-third of the intercept temperature coefficient has an effect on the glucose temperature coefficient (the effect of temperature on the temperature coefficient of the glucose concentration includes only one-third of the effect of temperature on the temperature coefficient of the intercept). At lower glucose concentrations, the effect of the intercept temperature coefficient on the glucose temperature coefficient is more visible. If the ratio of intercept to slope, Int/S, is 50 and the glucose concentration is 50 mg/dL, all of the intercept temperature coefficient has an effect on the glucose temperature coefficient (the effect of temperature on the temperature coefficient of the glucose concentration includes all of the effect of temperature on the temperature coefficient of the intercept). A smaller Int/S ratio reduces the effect of intercept temperature coefficient on the glucose temperature coefficient.

Figure 2:
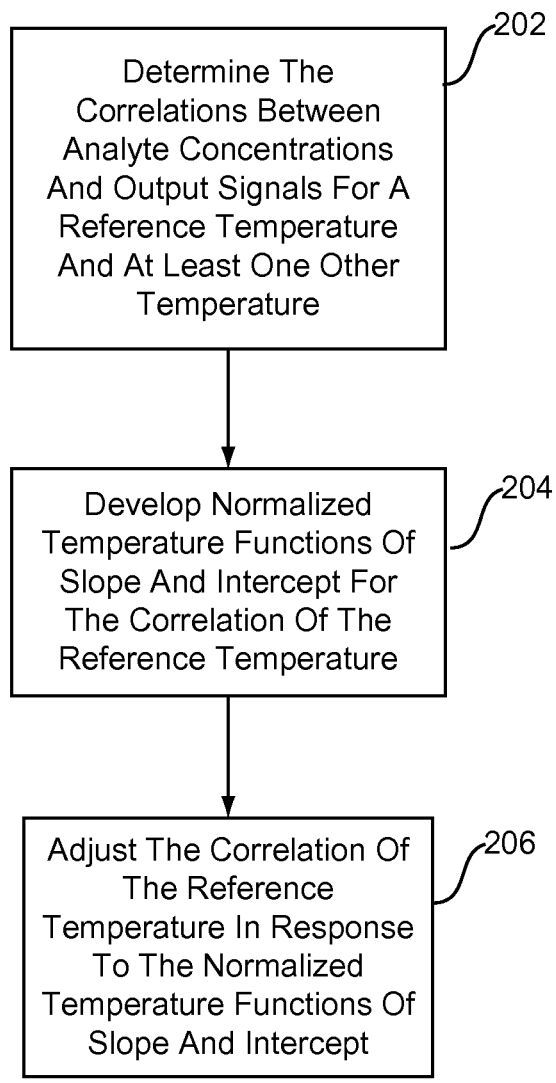
FIG. 2 represents a method for adjusting a correlation between analyte concentrations and output signals at a reference temperature in response to a sample temperature.

FIG. 2 represents a method for adjusting a correlation between analyte concentrations and output signals at a reference temperature in response to temperature. In 202, the correlations between analyte concentrations and output signals are determined for a reference temperature and at least one other temperature. In 204, normalized temperature functions are developed of slope and intercept for the correlation of the reference temperature. In 206, the correlation of the reference temperature is adjusted in response to the normalized temperature functions of slope and intercept. This method may be used with the method described in relation to FIG. 1, a similar method, or otherwise.

In 202 of FIG. 2, correlations between analyte concentrations and output signals are determined for a reference temperature and at least one other temperature. The output signals may be generated by an electrochemical reaction of the analyte in the sample as previously discussed. For each temperature, output signals are generated experimentally by electrochemical reactions at different analyte concentrations. The experimental results are analyzed to develop a correlation between the analyte concentrations and the output signals for each temperature.

Figure 3:
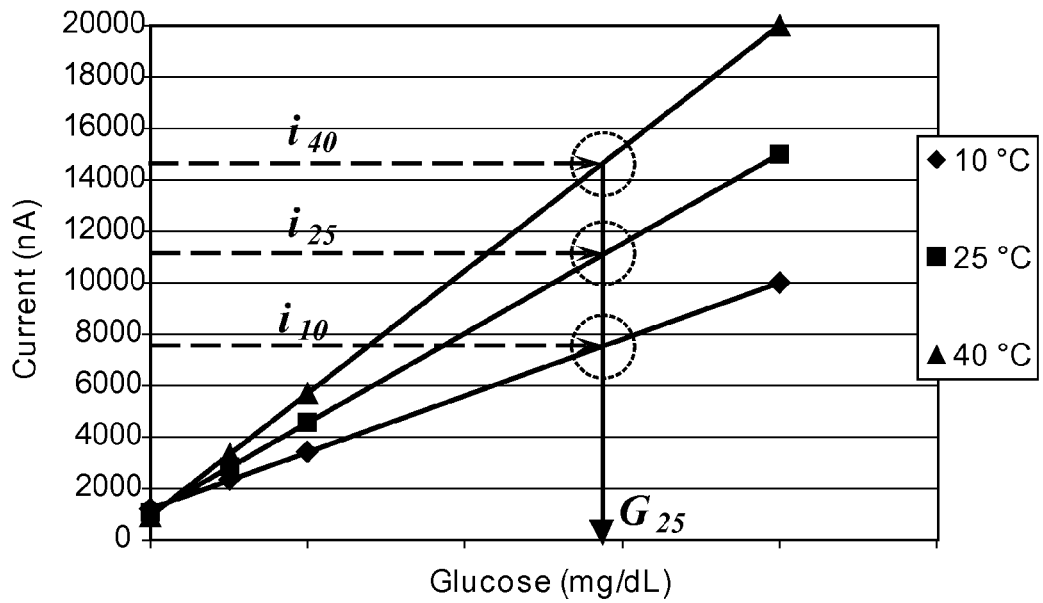
FIG. 3 is a graph illustrating correlations between analyte concentrations and output signals.

FIG. 3 is a graph illustrating correlations between analyte concentrations and output signals. In this illustration, each output signal is the current generated from an electrochemical reaction, such as gated amperometry. The analyte concentrations are glucose concentrations in whole blood. Correlations between current and glucose concentrations are graphically shown for a reference temperature of 25° C. and two other temperatures—10° C. and 40° C. While the correlation at 25° C. was selected as the reference temperature, correlations at other temperatures (including those not shown) may be selected as the reference temperature. While the illustration is directed toward particular features, such as the number of correlations, output signals, analyte concentrations, temperatures, and the like, the illustration is not meant to limit the scope, application, implementation, or the like.

Each of the graphical correlations is linear and may be represented by a correlation equation having a general form as follows:

$$G = \frac{I - Int}{S}. \quad (22)$$

Where G is the glucose concentration, I is the current, Int is the intercept of the correlation line with the y-axis, and S is the slope of the correlation line. While linear relationships are shown for the correlations between the glucose concentration and the current, other correlations may have other relationships, such as polynomial, exponential, trigonometric, a combination thereof, and the like.

In 204 of FIG. 2, normalized temperature functions are developed of slope and intercept for the correlation of the reference temperature. The temperature functions adjust the slope and intercept of the correlation for the reference temperature to the slope and intercept of a correlation for another temperature. The temperature-adjusted slope and intercept may be used to calculate the analyte or glucose concentration using an output signal or current generated at the other temperature.

To develop the temperature functions, the slopes and intercepts are normalized to the slope and intercept of the correlation for the reference temperature. The normalized slope of a correlation for a particular temperature is a unitless coefficient that adjusts the slope of the correlation for the reference temperature to the slope of the correlation for the particular temperature. The normalized intercept of a correlation for a particular temperature is a unitless coefficient that adjusts the intercept of the correlation for the reference temperature to the intercept of the correlation for the particular temperature. Both the normalized slope and normalized intercept of the correlation for the reference temperature are essentially one, indicating there is little or no adjustment to the slope and intercept of the correlation for the reference temperature. Other normalization methods may be used.

The normalized slopes of the correlations may be used to generate a temperature function of the slope, f(T), graphically and/or mathematically using a regression analysis or the like. The temperature function of the slope, f(T), from a regression analysis may be a second order polynomial such as follows:

$$f(T)=a_2 T^2+a_1 T+a_0 \quad (23)$$

Where T is the sample temperature and $a_2$, $a_1$, and $a_0$ are coefficients of a regression analysis representing the normalized slopes. While represented as a polynomial, the regression analysis may represent the temperature function of the slope, f(T), as another function.

The normalized intercepts of the correlations may be used to generate a temperature function of the intercept, g(T), graphically and/or mathematically using a regression analysis or the like. The temperature function of the intercept, g(T), from a regression analysis may be a second order polynomial such as follows:

$$g(T)=b_2 T^2+b_1 T+b_0 \quad (24)$$

Where T is the sample temperature and $b_2$, $b_1$, and $b_0$ are coefficients of a regression analysis representing the normalized intercepts. While represented as a polynomial, the regression analysis may represent the temperature function of the intercept, g(T), as another function.

FIG. 3 illustrates that correlations between current and glucose at 10° C., 25° C., and 40° C. calculate the same glucose concentration, $G_{25}$, from currents, $i_{40}$, $i_{25}$, and $i_{10}$, which are generated by electrochemical reactions of the analyte in the sample at those respective temperatures. The slopes and intercepts of the correlations may be normalized to the slope and intercept of the correlation for the reference temperature of 25° C. The normalized slopes and intercepts of the correlations may be used to generate the temperature function of the slope, f(T), and the temperature function of the intercept, g(T).

Figure 4:
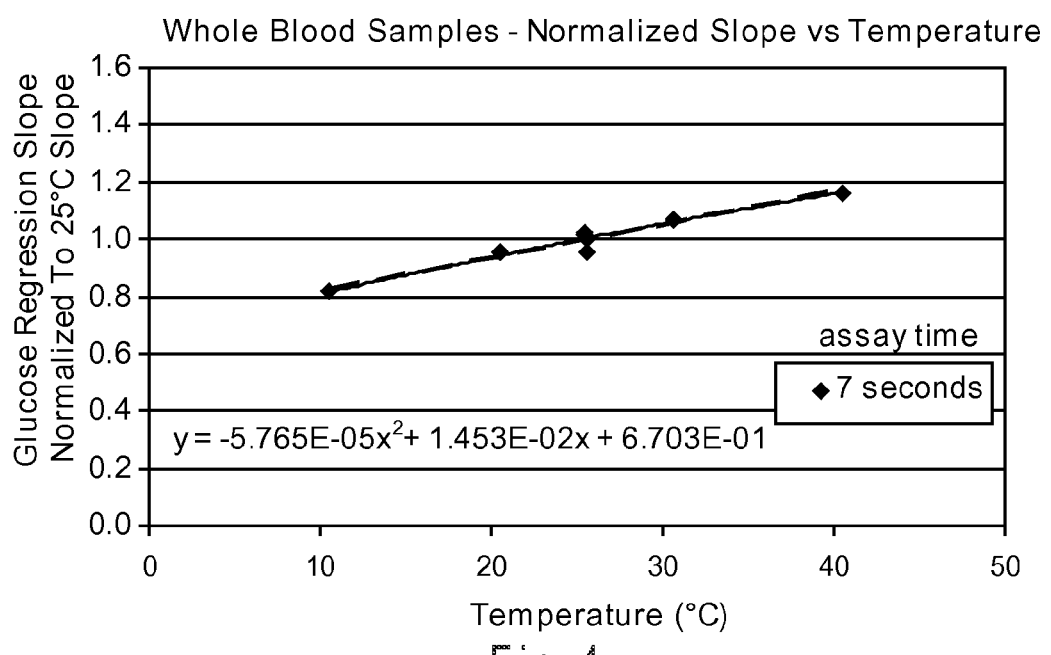
FIG. 4 is a graph illustrating normalized slopes as a function of temperature for correlations between glucose concentrations in whole blood and current for an assay time of 7 seconds.
Figure 5:
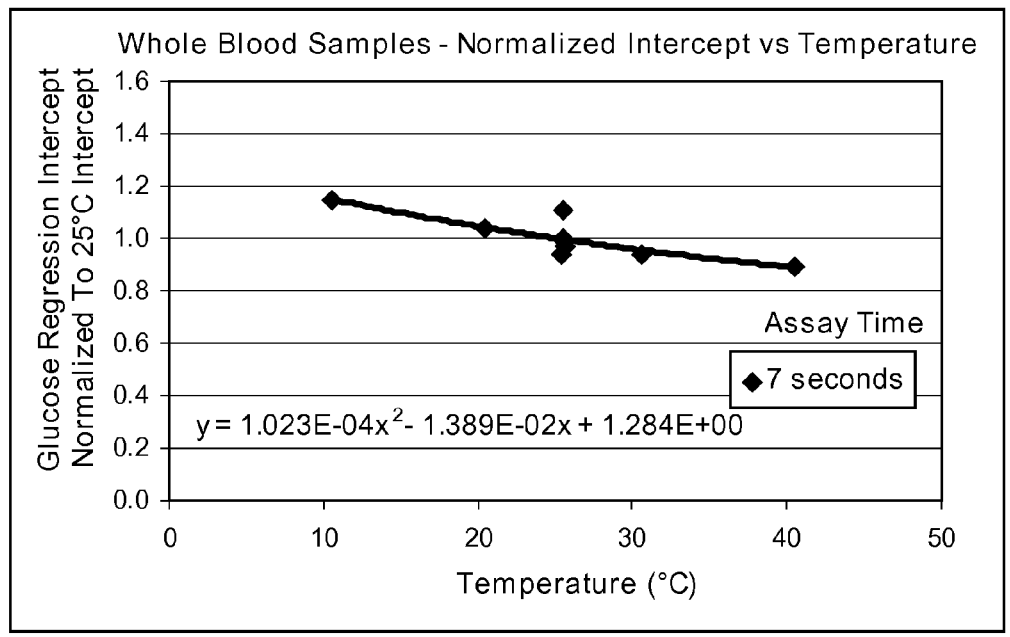
FIG. 5 is a graph illustrating normalized intercepts as a function of temperature for correlations between glucose concentrations in whole blood and current for an assay time of 7 seconds.

FIGS. 4 and 5 are graphs illustrating the normalized slopes and intercepts, respectively, as a function of temperature for correlations between glucose concentrations in whole blood and current. The correlations were generated from electrochemical reactions using gated amperometry with an assay time of 7 seconds (sec). The normalized slopes and intercepts are from correlations at 10° C., 20° C., 25° C., 30° C., and 40° C. The normalized slopes and intercepts were normalized to the slope and intercept of a correlation at a reference temperature of 25° C. While these illustrations are directed toward particular features such as normalized slopes, temperatures, and the like, the illustrations are not meant to limit the scope, application, implementation, or the like.

In FIG. 4, a regression analysis of the normalized slopes generates a temperature function of the slope, f(T), as follows:

$$f(T)=-0.00005765*T^2+0.01453*T+0.6703 \quad (25)$$

The temperature function of the slope, f(T), shown in equation (25) may be used to adjust the slope of the correlation for the reference temperature of 25° C. to the slope of a correlation for another temperature, such as a sample temperature. T is the other temperature. The temperature-adjusted slope may be used to calculate the glucose concentration using a current generated at the other temperature. Other temperature functions of the slope may be used.

In FIG. 5, a regression analysis of the normalized intercepts generates a temperature function of the intercept, g(T), as follows:

$$g(T)=0.0001023*T^2+0.01389*T+1.284 \quad (26)$$

The temperature function of the intercept, g(T), shown in equation (26) may be used to adjust the intercept of the correlation for the reference temperature of 25° C. to the intercept of a correlation for another temperature, such as a sample temperature. T is the other temperature. The temperature-adjusted intercept may be used to calculate the glucose concentration using a current generated at the other temperature. Other temperature functions for the intercept may be used.

The separate temperature functions for slope and intercept may be used with a program number assignment (PNA) table of the slope and intercept of the correlation for the reference temperature. In addition, the normalized slope and intercept provide a range in which the intrinsic temperature properties of a biosensor system may be independent of the output signal or current magnitude generated by the electrochemical reaction. The intrinsic temperature properties usually depend on the sensor strip design and manufacturing. A biosensor system may change the temperature functions and/or correlation equation (s) in response to the sensor strip type and batch used. The temperature function and correlation equation changes may be made by changing PNA table when a different or new sensor strip is used.

Figure 6:
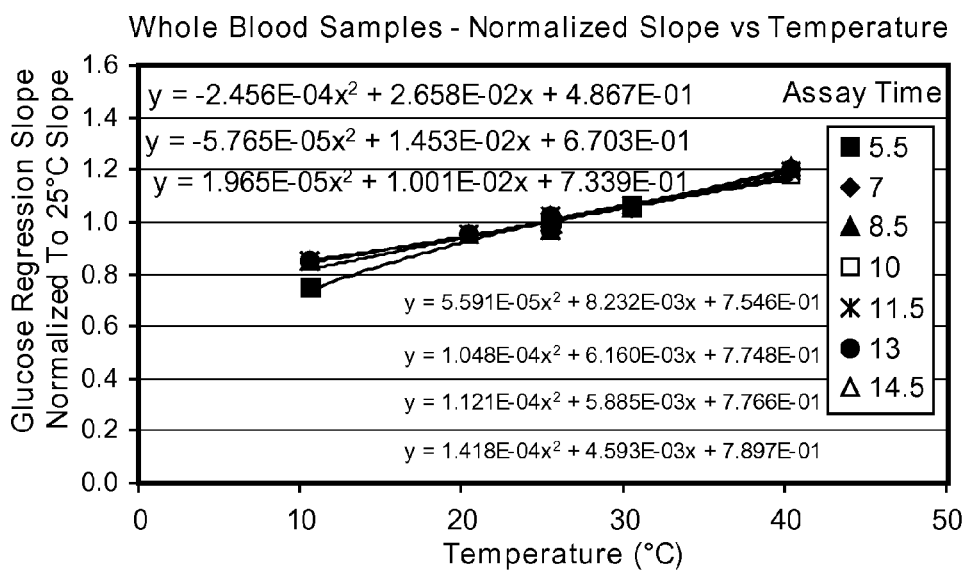
FIG. 6 is a graph illustrating the normalized slopes as a function of temperature for correlations between glucose concentrations in whole blood and current for several assay times.
Figure 7:
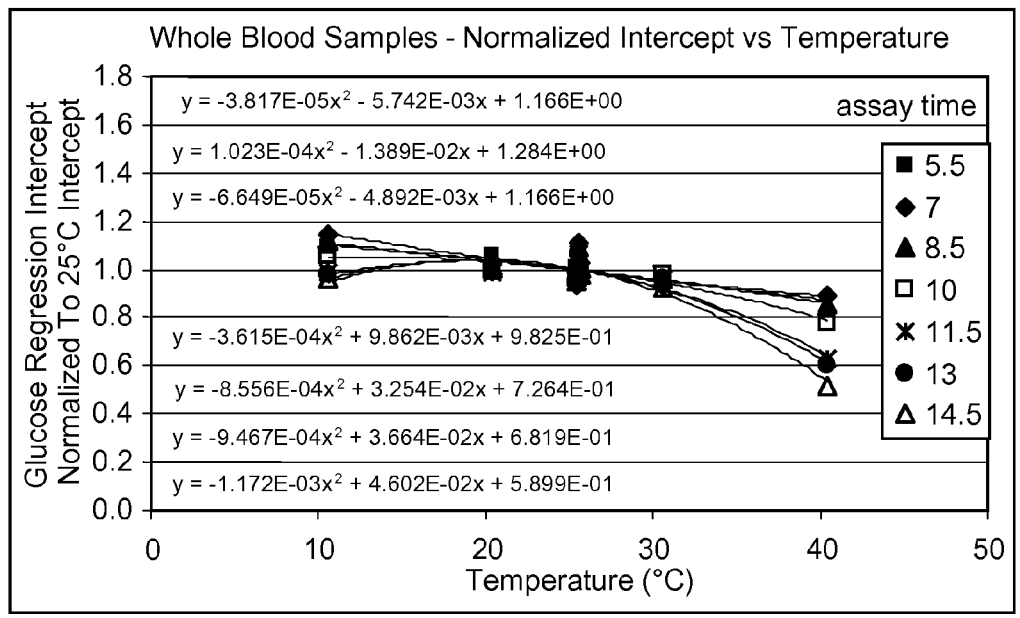
FIG. 7 is a graph illustrating the normalized intercepts as a function of temperature for correlations between glucose concentrations in whole blood and current for several assay times.

FIGS. 6 and 7 are graphs illustrating the normalized slopes and intercepts, respectively, as a function of temperature for correlations between glucose concentrations in whole blood and current. The correlations were generated from electrochemical reactions using gated amperometry with assay times of 5.5 sec, 7 sec, 8.5 sec, 10 sec, 11.5 sec, 13 sec, and 14.5 sec. The normalized slopes and intercepts are from correlations at 10° C., 20° C., 25° C., 30° C., and 40° C. The normalized slopes and intercepts were normalized to the slope and intercept of a correlation at a reference temperature of 25° C. While these illustrations are directed toward particular features, such as normalized slopes, temperatures, and the like, the illustrations are not meant to limit the scope, application, implementation, or the like.

FIGS. 6 and 7 illustrate normalized slopes and intercepts for electrochemical reactions using gated amperometry with multiple assay times. In determining temperature functions for normalized slopes and intercepts in electrochemical methods based on multiple pulses, there are multiple calibration points in the individual pulses of a pulse sequence. By using currents generated at different temperatures and different times in different pulses, slopes and intercepts from the different temperatures can be normalized to the slope and intercept at 25° C. The normalized slopes and intercepts may be represented graphically and/or mathematically as a function of temperature. The mathematical representation may be by a regression analysis that generates a second order polynomial. In multiple pulse methods, there may be many calibration points in a time range such as from 5.5 sec. to 7, 8.5, and 10 sec. Within this range, the intrinsic temperature property of a biosensor should be consistent if the reagents are sufficiently hydrated.

In FIG. 6, the temperature functions of the normalized slopes essentially overlap each other except for the 5.5 sec. assay time, which reflects the intrinsic consistency of the temperature sensitivity of the biosensor system. In addition, the temperature functions of the normalized slopes are quite symmetrical with respect to the reference temperature of 25° C. The normalized slopes at 10° C. are about 20% smaller than the normalized slope at 25° C. The normalized slopes at 40° C. are about 20% larger than the normalized slope at 25° C.

In FIG. 7, the temperature functions for normalized intercepts are very similar for assay times between 5.5 sec. and 10 sec. At longer times, the temperature effect on the normalized intercept becomes larger.

In 206 of FIG. 2, the correlation of the reference temperature is adjusted in response to the normalized temperature functions of slope and intercept. The correlation between analyte concentrations and output signals for the reference temperature is as follows:

$$G_R = \frac{i_R - Int_R}{S_R}. \tag{27}$$

Where $G_R$ is the analyte concentration at the reference temperature, $i_R$ is the output signal at the reference temperature, $Int_R$ is the intercept of the correlation for the reference temperature, and $S_R$ is the slope of the correlation for the reference temperature.

The correlation for the reference temperature represented by equation (27) may be adjusted in response to a sample temperature. Analyte concentrations at the reference temperature may be calculated using temperature-adjusted slopes and intercepts of the correlation for the reference temperature and output signals at a sample temperature, as follows:

$$G_R = \frac{i_T - Int_T}{S_T}. \tag{28}$$

Where $G_R$ is the analyte concentration at the reference temperature, $i_T$ is the output signal at the sample temperature, $Int_T$ is the intercept of the correlation for the reference temperature adjusted in response to the sample temperature, and $S_T$ is the slope of the correlation for the reference temperature adjusted for the sample temperature.

The slope of the correlation for the reference temperature adjusted in response to the sample temperature, $S_T$, may be calculated as follows:

$$S_T = S_R * f(T) \tag{29}$$

Where $S_R$ is the slope of the correlation for the reference temperature and f(T) is a temperature function that adjusts the slope for the sample temperature.

The intercept of the correlation for the reference temperature adjusted in response to the sample temperature, $Int_T$, may be calculated as follows:

$$Int_T = Int_R * g(T) \tag{30}$$

Where $Int_R$ is the intercept of the correlation for the reference temperature and g(T) is a temperature function that adjusts the intercept for the sample temperature.

The correlation for the reference temperature adjusted in response to a sample temperature as represented by equation (28) may be rewritten by substituting equations (29) and (30) for $S_T$ and $Int_T$, as follows:

$$G_R = \frac{i_T - (Int_R * g(T))}{(S_R * f(T))}. \tag{31}$$

Where $G_R$ is the analyte concentration at the reference temperature, $i_T$ is the output signal at the sample temperature, $Int_R$ is the intercept for the correlation of the reference temperature, g(T) is the normalized temperature function for intercept, $S_R$ is the slope for the correlation of the reference temperature, and f(T) is the normalized temperature function for slope.

The correlation for the reference temperature adjusted in response to a sample temperature as represented by equation (31) may be rewritten for use with the examples illustrated in FIGS. 3-5, as follows:

$$G_{25} = \frac{i_T - (Int_{25} * (-0.00005765 * T^2 + 0.01453 * T + 0.6703))}{(S_{25} * (0.0001023 * T^2 + 0.01389 * T + 1.284))}. \tag{32}$$

Where $G_{25}$ is the analyte concentration at the reference temperature of 25° C., $i_T$ is the output signal at the sample temperature, $Int_{25}$ is the intercept of the correlation for the reference temperature of 25° C., $S_{25}$ is the slope of the correlation for the reference temperature of 25° C., and T is the sample temperature.

Figure 8:
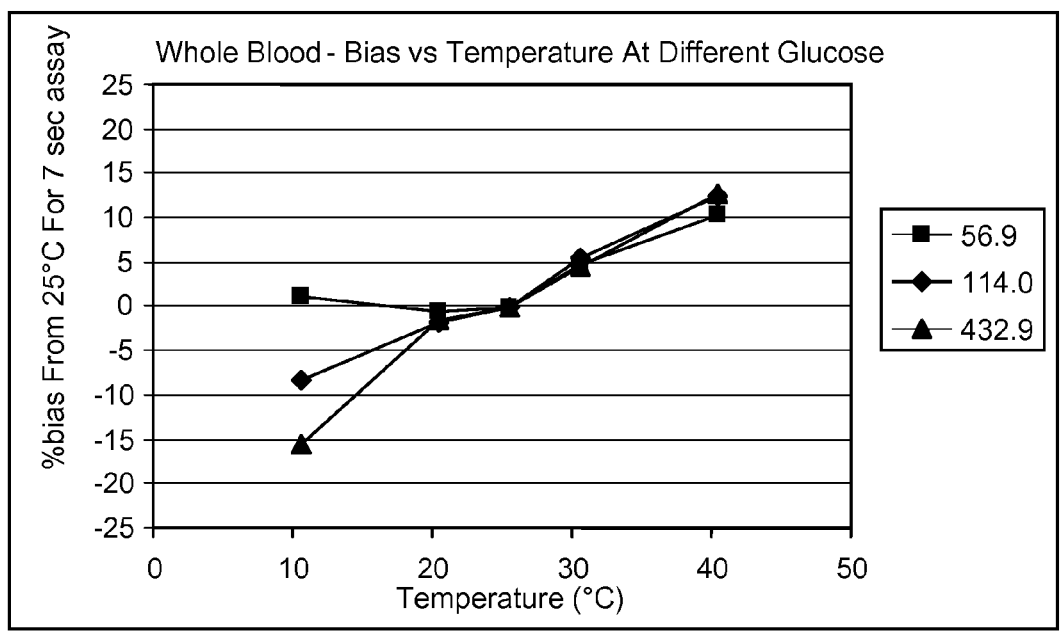
FIG. 8 is a graph illustrating the bias from a reference temperature of calculated glucose concentrations without any adjustment for temperature.
Figure 9:
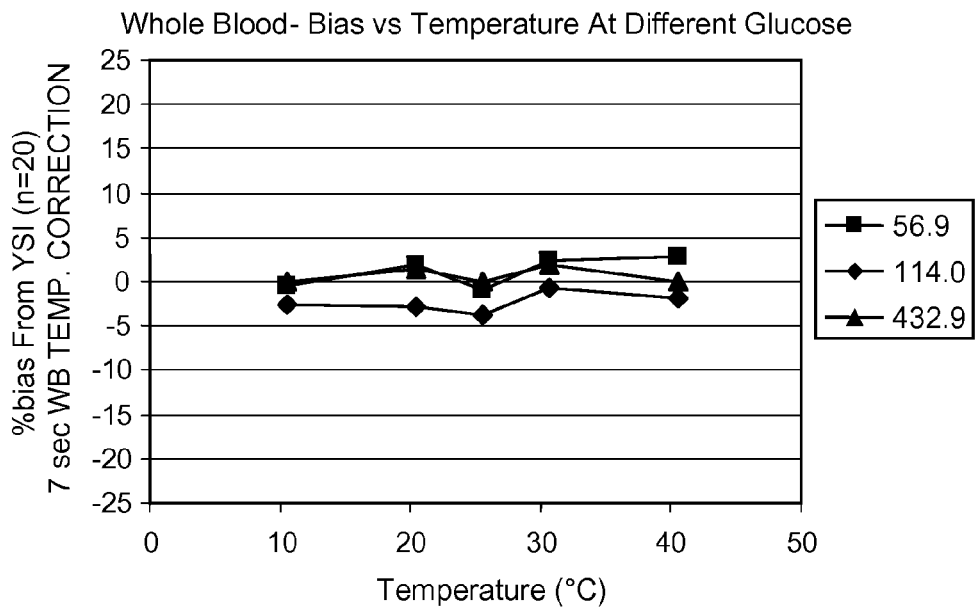
FIG. 9 is a graph illustrating the bias from a reference temperature of calculated glucose concentrations with adjustment for temperature.

FIGS. 8 and 9 are graphs illustrating the glucose bias values from a reference temperature as a function of temperature. FIG. 8 is a graph illustrating the bias of calculated glucose concentrations without any adjustment for temperature. FIG. 9 is a graph illustrating the bias of calculated glucose concentrations with adjustment for temperature as described previously. These graphs illustrate the percent bias from a reference temperature of 25° C. for plasma glucose concentrations of 56.9 mg/dL, 114.0 mg/dL, and 432.9 mg/dL in whole blood. The analysis was generated from electrochemical reactions using gated amperometry with an assay time of 7 sec at sample temperatures of 10° C., 20° C., 25° C., 30° C., and 40° C. While the illustrations are directed toward particular features such as temperatures, glucose concentrations, and the like, the illustrations are not meant to limit the scope, application, implementation, or the like.

In FIGS. 8 and 9, the percent bias values at 10° C., 20° C., and 25° C. for the 56.9 mg/dL glucose concentration show little if any change after the temperature adjustment, especially the percent bias value at 10° C. FIG. 8 indicates that the glucose concentrations from a correlation without temperature compensation generally have a negative bias at temperatures below the reference temperature of 25° C. FIG. 8 also indicates that glucose concentrations from a correlation without temperature adjustment generally have a positive bias at temperatures above the reference temperature of 25° C. FIG.

9 indicates that the percent bias values converge to a narrower range of about +/−5 percent when correlations with the temperature adjustment are used.

The temperature coefficient function of any particular parameter may be used to further show the internal consistency of the temperature function for adjusting correlation equations between analyte concentrations and output signals. The temperature coefficient (the intrinsic property) of the output signal, OS, may be defined as follows:

$$\alpha_{OS} = \frac{\partial OS/OS}{\partial T} = \frac{\partial \ln(OS)}{\partial T}. \quad (33)$$

Where $\alpha_{OS}$, is the temperature coefficient of the output signal, OS is the output signal, and T is temperature.

Figure 10:
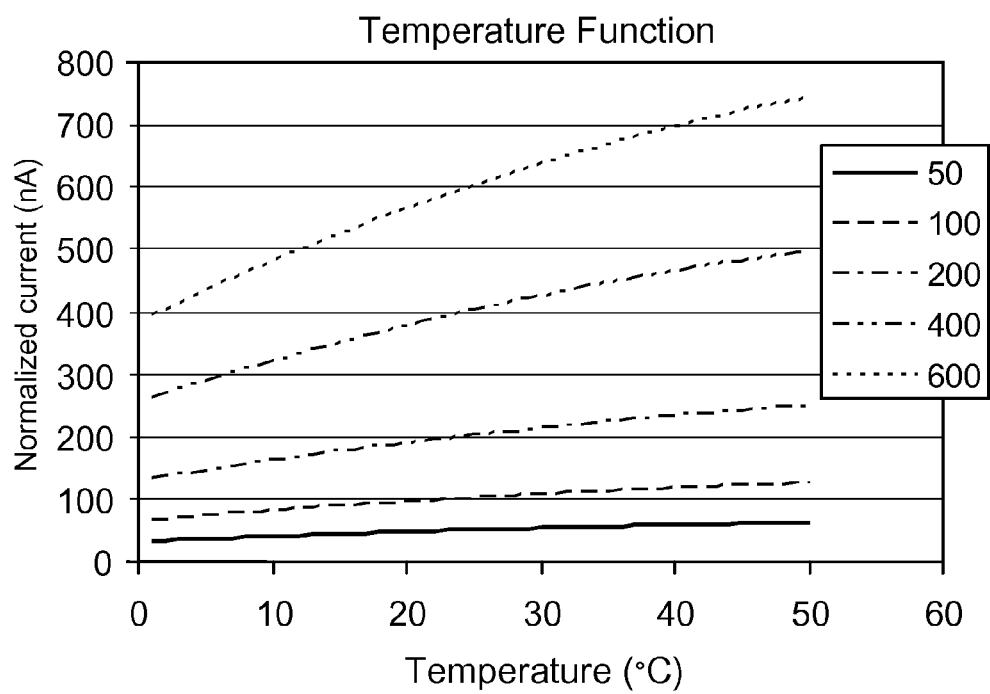
FIG. 10 is a graph illustrating the temperature function of current from a glucose sensor with normalized slope and intercept.
Figure 11:
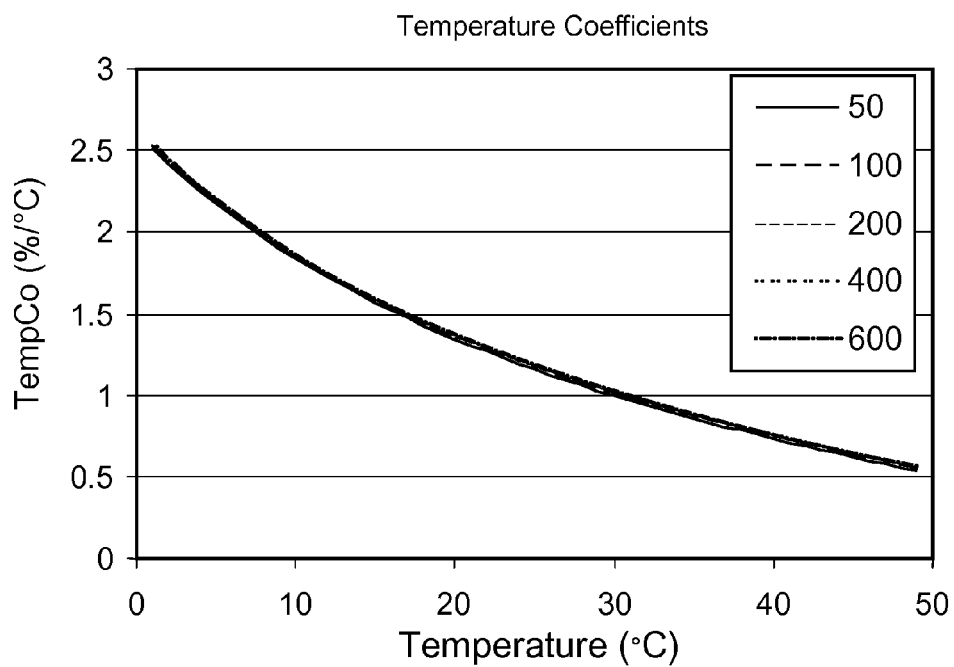
FIG. 11 is a graph illustrating the temperature coefficient function for the normalized current of FIG. 10 in relation to temperature.

FIGS. 10 and 11 are graphs illustrating the effect on the temperature coefficient function of the temperature-adjusted correlation equations between analyte concentrations and output signals. FIG. 10 illustrates the temperature function of current from a glucose sensor with normalized slope and intercept. FIG. 11 illustrates the temperature coefficient function for the normalized current of FIG. 10 in relation to temperature. The normalized current and temperature coefficients (TempCo) are in response to glucose concentrations of 50 mg/dL, 100 mg/dL, 200 mg/dL, 400 mg/dL, and 600 mg/dL. In FIG. 10, the current at 25° C. should be equal to the glucose value according to equation (5) for the normalized slope and intercept. FIG. 11 indicates that the temperature coefficients are functions of temperature—the lower the temperature, the higher the temperature coefficient. Within the temperature range of about 10° C. through about 40° C., the temperature coefficient ranges from about 1.85%/° C. through about 0.75%/° C. In addition, the temperature coefficient functions are independent of glucose concentration. While the illustrations are directed toward particular features such as temperature, glucose concentrations, and the like, the illustrations are not meant to limit the scope, application, implementation, or the like.

Figure 12:
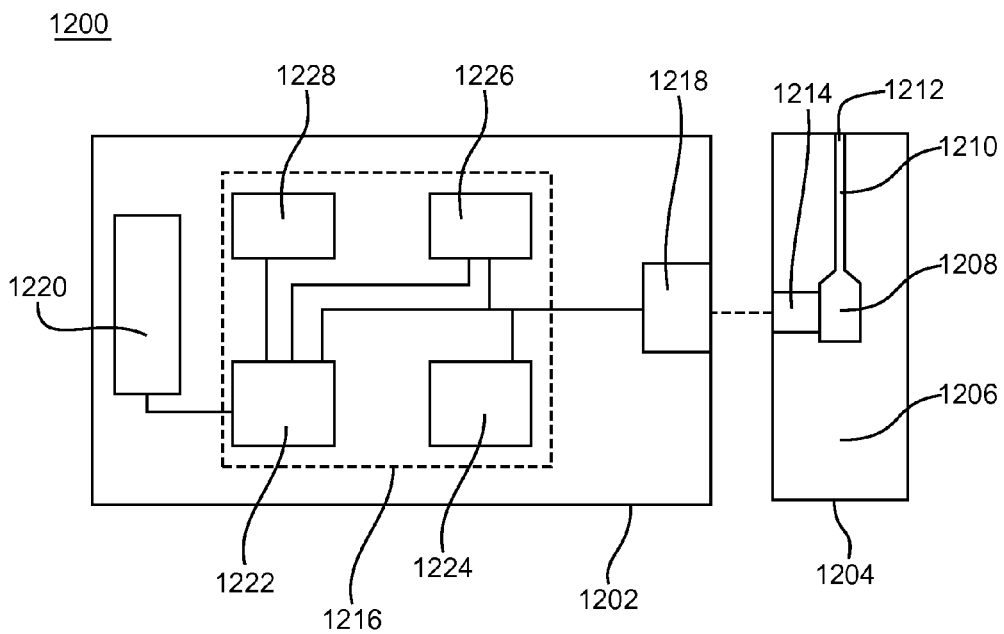
FIG. 12 depicts a schematic representation of a biosensor that determines an analyte concentration in a sample of a biological fluid.

FIG. 12 depicts a schematic representation of a biosensor 1200 that determines an analyte concentration in a sample of a biological fluid. Biosensor 1200 includes a measuring device 1202 and a sensor strip 1204, which may be implemented as a bench-top device, a portable or hand-held device, or the like. The measuring device 1202 and the sensor strip 1204 may be adapted to implement an electrochemical sensor system, an optical sensor system, a combination thereof, or the like. The biosensor 1200 adjusts a correlation for determining analyte concentrations from output signals at one temperature to determining analyte concentrations from output signals at other temperatures, such as a sample temperature as previously discussed. The temperature-adjusted correlations improve the accuracy and precision of the biosensor 1200 in determining the analyte concentration of the sample. The biosensor 1200 may be utilized to determine analyte concentrations, including those of glucose, uric acid, lactate, cholesterol, bilirubin, and the like. While a particular configuration is shown, the biosensor 1200 may have other configurations, including those with additional components.

The sensor strip 1204 has a base 1206 that forms a reservoir 1208 and a channel 1210 with an opening 1212. The reservoir 1208 and the channel 1210 may be covered by a lid with a vent. The reservoir 1208 defines a partially-enclosed volume (the cap-gap). The reservoir 1208 may contain a composition that assists in retaining a liquid sample such as water-swellable polymers or porous polymer matrices. Reagents may be deposited in the reservoir 1208 and/or channel 1210. The reagents may include one or more enzymes, binders, mediators, and like species. The reagents may include a chemical indicator for an optical system. The sensor strip 1204 also may have a sample interface 1214 disposed adjacent to the reservoir 1208. The sample interface 1214 may partially or completely surround the reservoir 1208. The sensor strip 1204 may have other configurations.

In an optical sensor system, the sample interface 1214 has an optical portal or aperture for viewing the sample. The optical portal may be covered by an essentially transparent material. The sample interface may have optical portals on opposite sides of the reservoir 1208.

In an electrochemical system, the sample interface 1214 has conductors connected to a working electrode and a counter electrode. The electrodes may be substantially in the same plane. The electrodes may be separated by greater than 200 or 250 μm and may be separated from the lid by at least 100 μm. The electrodes may be disposed on a surface of the base 1206 that forms the reservoir 1208. The electrodes may extend or project into the cap-gap formed by the reservoir 1208. A dielectric layer may partially cover the conductors and/or the electrodes. The sample interface 1214 may have other electrodes and conductors.

The measuring device 1202 includes electrical circuitry 1216 connected to a sensor interface 1218 and a display 1220. The electrical circuitry 1216 includes a processor 1222 connected to a signal generator 1224, a temperature sensor 1226, and a storage medium 1228.

The signal generator 1224 provides an electrical input signal to the sensor interface 1218 in response to the processor 1222. In optical systems, the electrical input signal may be used to operate or control the detector and light source in the sensor interface 1218. In electrochemical systems, the electrical input signal may be transmitted by the sensor interface 1218 to the sample interface 1214 to apply the electrical input signal to the sample of the biological fluid. The electrical input signal may be a potential or current and may be constant, variable, or a combination thereof, such as when an AC signal is applied with a DC signal offset. The electrical input signal may be applied as a single pulse or in multiple pulses, sequences, or cycles. The signal generator 1224 also may record an output signal from the sensor interface as a generator-recorder.

The temperature sensor 1226 determines the temperature of the sample in the reservoir of the sensor strip 1204. The temperature of the sample may be measured, calculated from the output signal, or assumed to be the same or similar to a measurement of the ambient temperature or the temperature of a device implementing the biosensor system. The temperature may be measured using a thermister, thermometer, or other temperature sensing device. Other techniques may be used to determine the sample temperature.

The storage medium 1228 may be a magnetic, optical, or semiconductor memory, another computer readable storage device, or the like. The storage medium 1228 may be a fixed memory device or a removable memory device such as a memory card.

The processor 1222 implements the analyte analysis and data treatment using computer readable software code and data stored in the storage medium 1228. The processor 1222 may start the analyte analysis in response to the presence of sensor strip 1204 at the sensor interface 1218, the application of a sample to the sensor strip 1204, in response to user input, or the like. The processor 1222 directs the signal generator 1224 to provide the electrical input signal to the sensor interface 1218. The processor 1222 receives the sample temperature from the temperature sensor 1226. The processor 1222 receives the output signal from the sensor interface 1218. The output signal is generated in response to the redox reaction of the analyte in the sample. The output signal may be generated using an optical system, an electrochemical system, or the like. The processor 1222 determines analyte concentrations from output signals at a sample temperature using a temperature-adjusted correlation equation for a reference temperature as previously discussed. The results of the analyte analysis are output to the display 1220 and may be stored in the storage medium 1228.

The correlation equations between analyte concentrations and output signals may be represented graphically, mathematically, a combination thereof, or the like. The correlation equations may be represented by a program number (PNA) table, another look-up table, or the like that is stored in the storage medium 1228. Instructions regarding implementation of the analyte analysis may be provided by the computer readable software code stored in the storage medium 1228. The code may be object code or any other code describing or controlling the functionality described herein. The data from the analyte analysis may be subjected to one or more data treatments, including the determination of decay rates, K constants, slopes, intercepts, and/or sample temperature in the processor 1222.

In electrochemical systems, the sensor interface 1218 has contacts that connect or electrically communicate with the conductors in the sample interface 1214 of the sensor strip 1204. The sensor interface 1218 transmits the electrical input signal from the signal generator 1224 through the contacts to the connectors in the sample interface 1214. The sensor interface 1218 also transmits the output signal from the sample through the contacts to the processor 1222 and/or signal generator 1224.

In light-absorption and light-generated optical systems, the sensor interface 1218 includes a detector that collects and measures light. The detector receives light from the liquid sensor through the optical portal in the sample interface 1214. In a light-absorption optical system, the sensor interface 1218 also includes a light source such as a laser, a light emitting diode, or the like. The incident beam may have a wavelength selected for absorption by the reaction product. The sensor interface 1218 directs an incident beam from the light source through the optical portal in the sample interface 1214. The detector may be positioned at an angle such as 45° to the optical portal to receive the light reflected back from the sample. The detector may be positioned adjacent to an optical portal on the other side of the sample from the light source to receive light transmitted through the sample.

The display 1220 may be analog or digital. The display may be an LCD display adapted to displaying a numerical reading.

In use, a liquid sample for analysis is transferred into the cap-gap formed by the reservoir 1208 by introducing the liquid to the opening 1212. The liquid sample flows through the channel 1210 into the reservoir 1208, filling the cap-gap while expelling the previously contained air. The liquid sample chemically reacts with the reagents deposited in the channel 1210 and/or reservoir 1208.

The sensor strip 1204 is disposed adjacent to the measuring device 1202. Adjacent includes positions where the sample interface 1214 is in electrical and/or optical communication with the sensor interface 1218. Electrical communication includes the transfer of input and/or output signals between contacts in the sensor interface 1218 and conductors in the sample interface 1214. Optical communication includes the transfer of light between an optical portal in the sample interface 1214 and a detector in the sensor interface 1218. Optical communication also includes the transfer of light between an optical portal in the sample interface 1214 and a light source in the sensor interface 1218.

The processor 1222 receives the sample temperature from the temperature sensor 1226. The processor 1222 directs the signal generator 1224 to provide an input signal to the sensor interface 1218. In an optical system, the sensor interface 1218 operates the detector and light source in response to the input signal. In an electrochemical system, the sensor interface 1218 provides the input signal to the sample through the sample interface 1214. The processor 1222 receives the output signal generated in response to the redox reaction of the analyte in the sample as previously discussed.

The processor 1222 determines the analyte concentration of the sample. The measuring device adjusts the correlation between analyte concentrations and output signals at a reference temperature in response to the sample temperature. The analyte concentration is determined from the temperature-adjusted correlation and the output signal at the sample temperature. In 110, the analyte concentration is displayed and may be stored for future reference.

Without limiting the scope, application, or implementation, the methods and systems previously described may be implemented using the following algorithm:

Step 1: Turn on meter power
Step 2: Perform biosensor Self-test
Step 3: Perform standardization of biosensor electronics
Step 4: Measure temperature, T
Step 5: Check temperature range
  if ($T>T_{Hi}$) then, Set Error Mode, "Temperature too high"
  if ($T<T_{Low}$) then, Set Error Mode, "Temperature too low"
Step 6: Apply input signal to sample
Step 7: Measure output signal, i
Step 8: Look up slope and intercept in program number assignment (PNA) table $S$=Slope value for current $Int$=Intercept for current Step 9: Adjust slope and intercept for temperature effect.

$$S_T = S^*(a_2^*T_1^2 + a_1^*T_1 + a_0)$$

$$Int_T = Int^*(b_2^*T_1^2 + b_1^*T_1 + b_0)$$

Step 10: Calculate glucose concentration at 25° C.

$$G_{25} = \frac{i_T - Int_T}{S_T}$$

Step 11: Check for extreme glucose levels
  if ($G_{25}>G_{max}$) then, Set Error Mode, "Glucose too high"
Step 12: Display result A program number assignment (PNA) table that may be used in the algorithm is given in Table I below. The constants that may be used in the algorithm are given in Table II below. Other PNA tables and/or constants may be used.

TABLE I

| PNA # | code table # | slope of column 8.028 intercept | PNA # | code table # | slope of column 8.498 intercept | PNA # | code table # | slope of column 8.995 intercept | PNA # | code table # | slope of column 9.522 intercept |
|---|---|---|---|---|---|---|---|---|---|---|---|
| 1  | 1  | 310.04 | 18 | 18 | 310.62 | 34 | 35 | 311.24 | 49 | 52 | 311.90 |
| 2  | 2  | 330.11 | 19 | 19 | 331.87 | 35 | 36 | 333.73 | 50 | 53 | 335.71 |
| 3  | 3  | 350.18 | 20 | 20 | 353.11 | 36 | 37 | 356.22 | 51 | 54 | 359.51 |
| 4  | 4  | 370.25 | 21 | 21 | 374.36 | 37 | 38 | 378.71 | 52 | 55 | 383.32 |
| 5  | 5  | 390.32 | 22 | 22 | 395.60 | 38 | 39 | 401.20 | 53 | 56 | 407.12 |
| 6  | 6  | 410.39 | 23 | 23 | 416.85 | 39 | 40 | 423.69 | 54 | 57 | 430.92 |
| 7  | 7  | 430.46 | 24 | 24 | 438.09 | 40 | 41 | 446.17 | 55 | 58 | 454.73 |
| 8  | 8  | 450.53 | 25 | 25 | 459.34 | 41 | 42 | 468.66 | 56 | 59 | 478.53 |
| 9  | 9  | 470.60 | 26 | 26 | 480.58 | 42 | 43 | 491.15 | 57 | 60 | 502.34 |
| 10 | 10 | 490.67 | 27 | 27 | 501.83 | 43 | 44 | 513.64 | 58 | 61 | 526.14 |
| 11 | 11 | 510.74 | 28 | 28 | 523.07 | 44 | 45 | 536.13 | 59 | 62 | 549.95 |
| 12 | 12 | 530.81 | 29 | 29 | 544.32 | 45 | 46 | 558.62 | 60 | 63 | 573.75 |
| 13 | 13 | 550.88 | 30 | 30 | 565.56 | 46 | 47 | 581.11 | 61 | 64 | 597.56 |
| 14 | 14 | 570.95 | 31 | 31 | 586.81 | 47 | 48 | 603.59 | 62 | 65 | 621.36 |
| 15 | 15 | 591.02 | 32 | 32 | 608.05 | 48 | 49 | 626.08 |    | 66 |        |
| 16 | 16 | 611.09 | 33 | 33 | 629.30 |    | 50 |        |    | 67 |        |
| 17 | 17 | 631.16 |    | 34 |        |    | 51 |        |    | 68 |        |

TABLE II

| CONSTANT | DESCRIPTION | VALUE | UNITS |
|---|---|---|---|
| $T_{HI}$ | Invalid Temperature High | 50 | °C. |
| $T_{LO}$ | Invalid Temperature Low | 5 | °C. |
| $a_2$ | coefficient, slope temperature function | -5.765e-5 | — |
| $a_1$ | coefficient, slope temperature function | 0.01453 | — |
| $a_o$ | coefficient, slope temperature function | 0.6703 | — |
| $b_2$ | coefficient, intercept temperature function | 1.023 | — |
| $b_1$ | coefficient, intercept temperature function | -0.01389 | — |
| $b_o$ | coefficient, intercept temperature function | 1.284 | — |
| $G_{max}$ | maximum allowable glucose concentration | 1500 | mg/dL |

While various embodiments of the invention have been described, it will be apparent to those of ordinary skill in the art that other embodiments and implementations are possible within the scope of the invention.

What is claimed is:

1. A method for determining an analyte concentration in a sample of a biological fluid, comprising:
   determining a sample temperature of the sample;
   generating an output signal in response to a redox reaction of an analyte in the sample;
   adjusting a correlation between output signals at a reference temperature and analyte concentrations, to a temperature-adjusted correlation between output signals at the sample temperature and analyte concentrations, in response to the sample temperature; and
   after adjusting the correlation, determining the analyte concentration in the sample from the temperature-adjusted correlation and the output signals at the sample temperature.

2. The method of claim 1, further comprising adjusting the correlation in response to a normalized temperature function of slope and a normalized temperature function of intercept.

3. The method of claim 1, where the temperature-adjusted correlation between analyte concentrations and output signals is represented as follows:

$$A_R = \frac{OS_T - Int_T}{S_T},$$

where $A_R$ is the analyte concentration at the reference temperature, $OS_T$ is the output signal at the sample temperature, $Int_T$ is an intercept of the correlation at the reference temperature adjusted by a normalized temperature function for intercept, and $S_T$ is a slope of the correlation at the reference temperature adjusted by a normalized temperature function for slope.

4. The method of claim 3, where the normalized temperature function for slope comprises a regression analysis of normalized slopes.

5. The method of claim 4, where the normalized temperature function for slope, f(T), is represented as follows:

$$f(T) = a_2 T^2 + a_1 T + a_0,$$

where T is the sample temperature and $a_2$, $a_1$, and $a_0$ are coefficients of a regression analysis representing the normalized slopes.

6. The method of claim 3, where the normalized temperature function for intercept comprises a regression analysis of normalized intercepts.

7. The method of claim 6, where the normalized temperature function for intercept, g(T) is represented as follows:

$$g(T) = b_2 T^2 + b_1 T + b_0,$$

where T is the sample temperature and $b_2$, $b_1$, and $b_0$ are coefficients of a regression analysis representing the normalized intercepts.

8. The method of claim 1, further comprising generating the output signal in response to an electrochemical process.

9. The method of claim 1, where the output signal comprises light.

10. The method of claim 1, where the output signal comprises an electrical signal.

11. The method of claim 1, further comprising generating the output signal in response to pulsed input signals.

12. The method of claim 1, where the analyte comprises glucose and the biological fluid comprises whole blood.

13. The method of claim 1, where determining a sample temperature of the sample comprises measuring the sample temperature, calculating the sample temperature from the output signal, or measuring an ambient temperature and assuming the sample temperature to be the same or similar to the ambient temperature.

14. A biosensor for determining an analyte concentration in a biological fluid, comprising:
- a measuring device having a processor connected to a sensor interface and a temperature sensor; and
- a sensor strip having a reservoir for a liquid sample, and a sample interface in communication with the sensor interface;
- where the processor adjusts a correlation between output signals at a reference temperature and analyte concentrations, to a temperature-adjusted correlation between output signals at a sample temperature and analyte concentrations, in response to a sample temperature from the temperature sensor; and
- where, after the processor adjusts the correlation, the processor determines an analyte concentration in a sample of a biological fluid in the reservoir of the sensor strip from the temperature-adjusted correlation and an output signal from the sample.

15. The biosensor of claim 14, where the processor adjusts the correlation in response to a normalized temperature function of slope and a normalized temperature function of intercept.

16. The biosensor of claim 14 where the temperature-adjusted correlation is represented as follows:

$$G_R = \frac{i_T - (Int_R * g(T))}{(S_R * f(T))},$$

where $G_R$ is an analyte concentration at the reference temperature, $i_T$ is the output signal at a sample temperature, $Int_R$ is an intercept of the correlation for the reference temperature, $g(T)$ is a normalized temperature function for intercept, $S_R$ is a slope of the correlation for the reference temperature, and $f(T)$ is a normalized temperature function for slope.

17. The biosensor of claim 16, where the normalized temperature function for slope, f(T), is represented as follows:

$$f(T)=a_2T^2+a_1T+a_0,$$

where T is the sample temperature and $a_2$, $a_1$, and $a_0$ are coefficients of a regression analysis representing normalized slopes.

18. The biosensor of claim 16, where the normalized temperature function for intercept, g(T) is represented as follows:

$$g(T)=b_2T^2+b_1T+b_0,$$

where T is the sample temperature and $b_2$, $b_1$, and $b_0$ are coefficients of a regression analysis representing normalized intercepts.

19. The biosensor of claim 14, where the output signal comprises light.

20. The biosensor of claim 14, where the output signal comprises an electrical signal.

21. The biosensor of claim 14, where the output signal is responsive to pulsed input signals.

22. The biosensor of claim 14, where the analyte comprises glucose and the biological fluid comprises whole blood.

23. The biosensor of claim 14, where the sample temperature is determined by measuring the sample temperature, by calculating the sample temperature from the output signal, or by measuring an ambient temperature and assuming the sample temperature to be the same or similar to the ambient temperature.

* * * * *